(12) United States Patent
Xie et al.

(10) Patent No.: US 11,581,061 B2
(45) Date of Patent: Feb. 14, 2023

(54) HIGH-THROUGHPUT VIRTUAL DRUG SCREENING SYSTEM BASED ON MOLECULAR FINGERPRINTS AND DEEP LEARNING

(71) Applicant: GUANGDONG INSTITUTE OF MICROBIOLOGY (GUANGDONG DETECTION CENTER OF MICROBIOLOGY), Guangzhou (CN)

(72) Inventors: Liwei Xie, Guangzhou (CN); Zhihong Liu, Guangzhou (CN); Bingdong Liu, Guangzhou (CN); Xiaohan Pan, Guangzhou (CN); Mulan Han, Guangzhou (CN); Guohuan Xu, Guangzhou (CN)

(73) Assignee: GUANGDONG INSTITUTE OF MICROBIOLOGY (GUANGDONG DETECTION CENTER OF MICROBIOLOGY), Guangzhou (CN)

( * ) Notice: Subject to any disclaimer, the term of this patent is extended or adjusted under 35 U.S.C. 154(b) by 368 days.

(21) Appl. No.: 16/772,843

(22) PCT Filed: Jan. 17, 2020

(86) PCT No.: PCT/CN2020/072584
§ 371 (c)(1),
(2) Date: Jun. 15, 2020

(87) PCT Pub. No.: WO2020/125812
PCT Pub. Date: Jun. 25, 2020

(65) Prior Publication Data
US 2021/0217487 A1     Jul. 15, 2021

(30) Foreign Application Priority Data
Mar. 26, 2019   (CN) .......................... 201910234195.9

(51) Int. Cl.
*G16B 15/30* (2019.01)
*G06N 3/04* (2006.01)
*G06N 3/08* (2006.01)

(52) U.S. Cl.
CPC ............... *G16B 15/30* (2019.02); *G06N 3/04* (2013.01); *G06N 3/08* (2013.01)

(58) Field of Classification Search
CPC .......... G16B 15/30; G16B 35/20; G06N 3/04; G06N 3/08
See application file for complete search history.

(56) References Cited

U.S. PATENT DOCUMENTS

| 6,295,514 B1 * | 9/2001 | Agrafiotis | ........................ 703/12 |
| 2013/0138478 A1 * | 5/2013 | Hyde | ..................... G06Q 30/02 |
| | | | 705/7.33 |

(Continued)

FOREIGN PATENT DOCUMENTS

| CN | 106446607 A | 2/2017 | |
| CN | 107862173 A | * 11/2017 | ............. G16C 20/30 |
| CN | 107862173 A | 3/2018 | |

OTHER PUBLICATIONS

"A New Graph-Based Molecular Descriptor Using the Canonical Representation of the Molecule", The Scientific World Journal vol. 2014, Article ID 286974, Hentabli et al.*

(Continued)

*Primary Examiner* — Qun Shen
(74) *Attorney, Agent, or Firm* — Bayramoglu Law Offices LLC

(57) ABSTRACT

A high-throughput virtual drug screening system based on molecular fingerprints and deep learning, includes a deep-learning model online-modeling subsystem and an online virtual-screening subsystem. The system combines the molecular fingerprints and a deep neural network method to construct a high-throughput virtual drug screening system.

(Continued)

The system includes built-in structural-diversity screening libraries and realizes the online automatic construction of deep learning models and virtual screening. The system helps researchers in the drug discovery industry such as medicinal chemistry to conduct rapid screening through their desired targets to obtain potential active compounds and accelerate drug discovery.

3 Claims, 3 Drawing Sheets

(56) References Cited

U.S. PATENT DOCUMENTS

| | | | |
|---|---|---|---|
| 2017/0173262 A1* | 6/2017 | Veltz | G16H 20/17 |
| 2018/0285731 A1 | 10/2018 | Heifets et al. | |
| 2019/0048306 A1* | 2/2019 | Brown | C12M 41/26 |
| 2021/0217487 A1* | 7/2021 | Xie | G16B 35/20 |

OTHER PUBLICATIONS

Wang Xiting et al., Screening anti-fibrosis Chinese Medicinal Compounds Based on Machine Learning, Journal of Beijing University of Traditional Chinese Medicine, Jan. 2019, pp. 30-35, vol. 42 No. 1.

Xiaoyan Li et al., Research on the Application of Multi Virtual Machine Collaborative Computing in Virtual Drug Screening, China Medical Herald, Jun. 2018, pp. 146-149, vol. 15 No. 16.

* cited by examiner

HIGH-THROUGHPUT VIRTUAL DRUG SCREENING SYSTEM BASED ON MOLECULAR FINGERPRINTS AND DEEP LEARNING

CROSS-REFERENCE TO THE RELATED APPLICATIONS

This application is the national phase entry of International Application No. PCT/CN2020/072584, filed on Jan. 17, 2020, which is based upon and claims priority to Chinese Patent Application No. 201910234195.9, filed on Mar. 26, 2019, the entire contents of which are incorporated herein by reference.

TECHNICAL FIELD

The present invention relates to the technical field of drug development, and particularly relates to a high-throughput virtual drug screening system based on molecular fingerprints and deep learning.

BACKGROUND

Drug development is a costly, risky and lengthy process. Generally, developing a drug takes more than 10 years and costs billions of dollars, which are increasing year by year. In recent years, deep learning technology has made major breakthroughs in several fields such as autonomous driving, voice recognition, and image recognition. Meanwhile, deep learning technology has also made important progress in the field of biomedicine; taking advantage of deep learning in image recognition, a series of deep learning-based diagnosis applications have been developed for diseases such as skin cancer, congenital cataracts and childhood autism. The pharmaceutical industry has begun to focus on the use of deep learning technology to accelerate drug development and reduce costs. Earlier studies have shown that deep learning technology has advantages in optimizing synthetic routes, predicting pharmacological properties of drugs, predicting drug targets, and virtual screening, as compared with traditional machine learning methods (such as random forests, support vector machines, and Bayesian models).

Drug screening is a key part of drug discovery. High-throughput virtual screening can greatly reduce the screening time and cost, and is of great significance for accelerating drug development. Virtual screening methods include structure-based virtual screening methods (molecular docking) and ligand-based virtual screening (similarity, pharmacophore, three-dimensional quantitative structure-activity relationship, and machine learning). Molecular fingerprints are a method of encoding chemical structures; initially the method was mainly used for similarity search of chemical structures, but later it is found that use of molecular fingerprints has a good effect in establishing drug activity, and thus the method has been widely used in structure-activity relationship studies.

SUMMARY

One object of the present invention is to provide a high-throughput virtual drug screening system based on molecular fingerprints and deep learning which can improve the efficiency and accuracy of drug screening.

The high-throughput virtual drug screening system based on molecular fingerprints and deep learning, comprises a deep-learning model online-modeling subsystem and an online virtual-screening subsystem;

the deep-learning model online-modeling subsystem comprises an online-modeling module and a model-result module;

the online-modeling module is configured to construct a corresponding model based on a type of the model to be constructed, a drug target, molecular fingerprints, and parameters, which are selected by a user, wherein the type of the model to be constructed includes a qualitative classification model and a quantitative regression model;

the model-result module is configured to indicate a model list and detailed information of an individual model, wherein the model list is configured to indicate information of all models submitted by the current user, including serial numbers of the models, data sources, serial numbers of drug targets, types of models, creation times and completion times of the models, and status of the models; the detailed information of an individual model includes parameters of the model and performance information of the model, which are configured to indicate changes during a model performance index training process;

the online virtual-screening subsystem comprises an online-screening module and a screening-result module;

the online-screening module is configured to select a screening model and a screening library and then conduct screening, wherein the screening model is selected by entering the serial number of the model or clicking within the model list, and the screening library is selected from existing compound libraries, or from compound libraries uploaded by the user; and the screening-result module is configured to store a screening list and screening detailed information, wherein the screening list is configured to indicate a serial number of the screening model, a name of the screening library, features of the screening model, and starting time and ending time of the screening, and the screening detailed information includes scores and serial numbers of selected compounds.

The present invention combines the molecular fingerprints and a deep neural network method to construct a high-throughput virtual drug screening system. The system includes built-in structural-diversity screening libraries and realizes the online automatic construction of deep learning models and virtual screening. The system is smooth and easy to use. It helps researchers of drug discovery industry such as medicinal chemistry to conduct rapid screening through their desired targets to obtain potential active compounds and accelerate drug discovery.

DETAILED DESCRIPTION OF THE EMBODIMENTS

Figure 1:
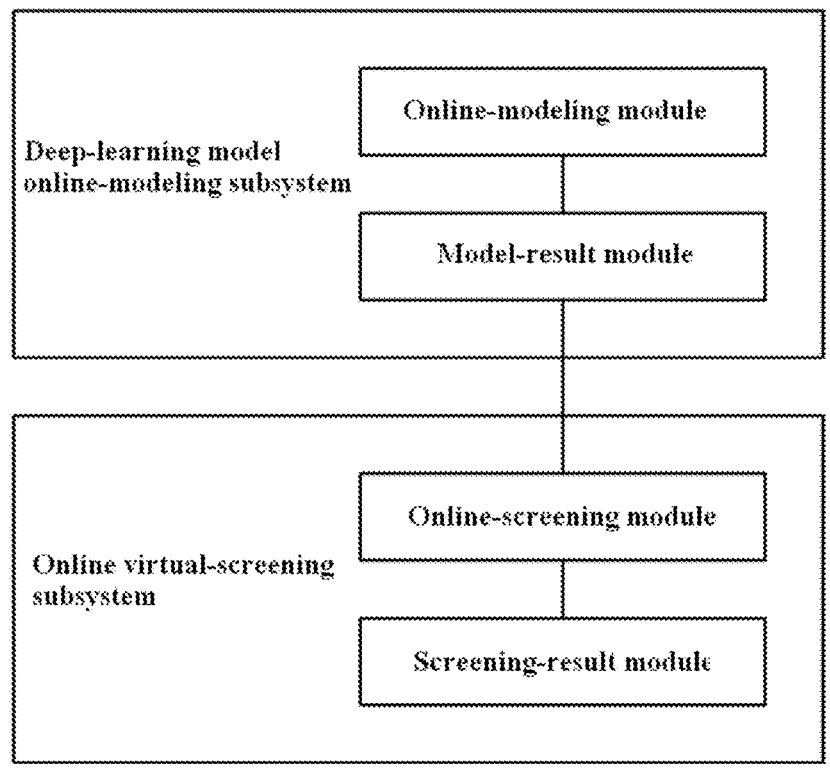
FIG. 1 is a schematic diagram showing a structure of the high-throughput virtual drug screening system based on molecular fingerprints and deep learning of the present invention.
Figure 2:
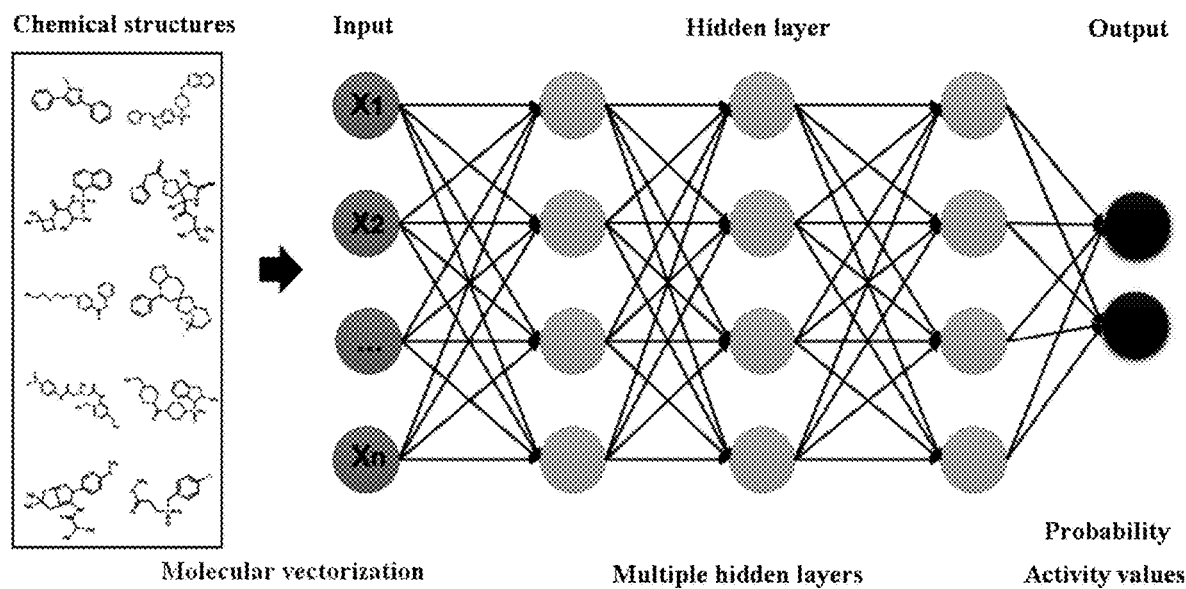
FIG. 2 is a schematic diagram showing a principle of the high-throughput virtual drug screening system based on molecular fingerprints and deep learning of the present invention.
Figure 3:
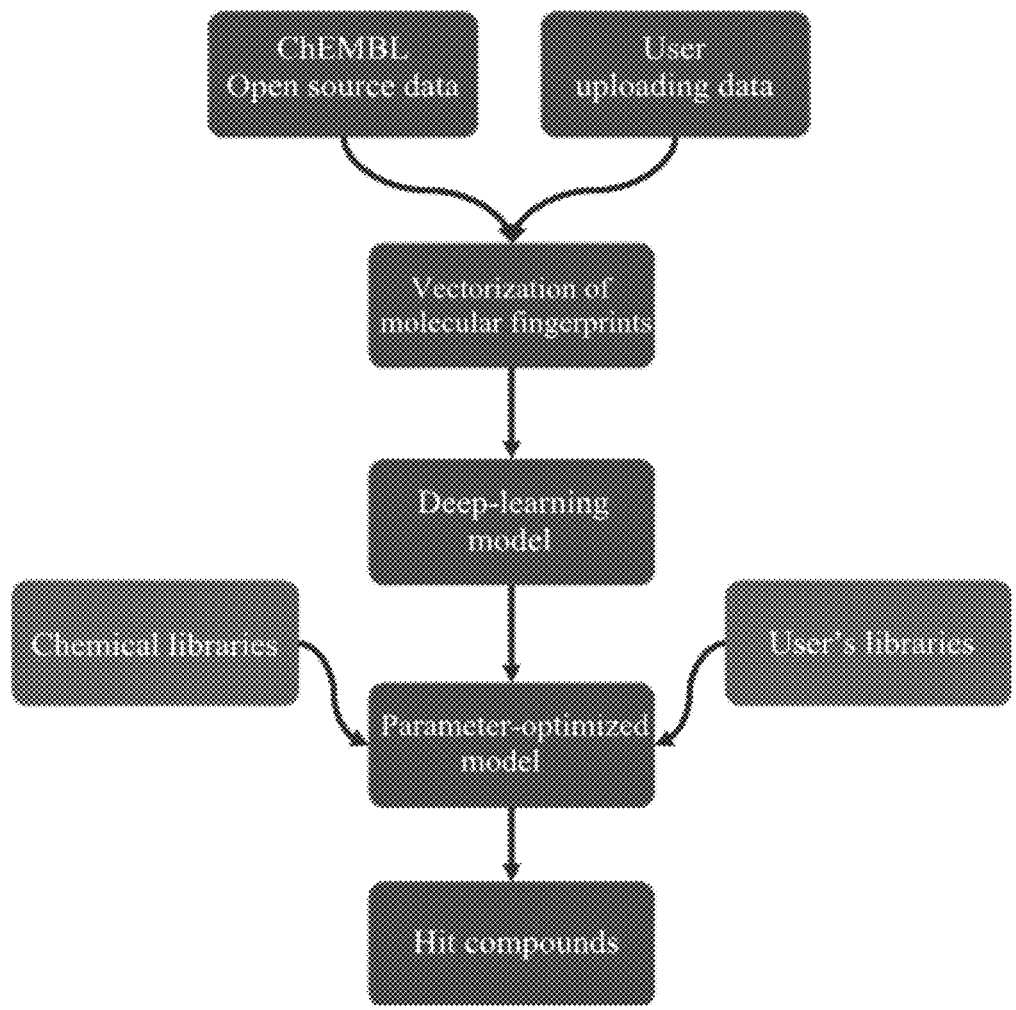
FIG. 3 is a schematic diagram showing a screening process of the high-throughput virtual drug screening system based on molecular fingerprints and deep learning of the present invention.

The present invention proposes a high-throughput virtual drug screening system based on molecular fingerprints and deep learning, which comprises a deep-learning model online-modeling subsystem and an online virtual-screening subsystem, and automates the entire process from the construction and training of deep-learning models to the virtual screening based on the models.

The deep-learning model online-modeling subsystem mainly comprises an online-modeling module and a model-result module.

Online-modeling module:

(1) Selecting the type of model, including a qualitative classification model and a quantitative regression model.

(2) Via a data preparation module, selecting a drug target for which the model is to be constructed based on the above type of model. Currently, the classification model is applicable for 1,251 drug targets, and the regression model is applicable for 1,814 drug targets. Meanwhile it is possible to upload users' data in sdf format.

(3) Selecting molecular fingerprints. The system involve the uses of twelve types of molecular fingerprints methods, including CDKFP, ExtFP, EStateFP, GraphFP, MACCSFP, PubchemFP, SubFP, SubFPC, KRFP, KRFPC, AP2D, and APC2D.

(4) Via a parameter selecting module, the user can set parameters as shown in the following list depending on the demand.

| Parameter | Value |
| --- | --- |
| Learning rate | 0.1, 0.01, 0.001 |
| Epochs | 30, 50, 100, 200 |
| Batch size | 16, 32, 64, 128, 256 |
| Hidden layers | 1,2, 3,4, 5, 6, 7, 8, 9, 10 |
| Number neurons | 10, 50, 100, 200, 500, 1000 |
| Activation function | ReLU, Sigmoid, Tanh |
| Dropout | 0, 10%, 20%, 50% |
| Loss function | MSELoss, cross_entropy |
| Output function | self or sigmoid |

Model-Result Module:

The model-result module includes a model list and an individual-model detailed-information module. The model list is configured to indicate information of all models submitted by the current user, including serial numbers of the models, data sources, serial numbers of drug targets, types of models, creation times and completion times of the models, and status of the models. The individual-model detailed-information module is configured to indicate parameters of the model and performance information of the model, and indicate changes during a model performance index training process. For a classification model, it is possible to indicate changes in loss, Accuracy, Recall, Precision, F1 score, Matthews correlation coefficient (MCC), and AUC value. For a regression model, it is possible to indicate changes in loss, coefficient of determination (R2), mean squared error (MSE), root mean squared error (RMSE), and mean absolute error (MAE).

The online virtual-screening subsystem mainly comprises an online-screening module and a screening-result module.

Online-Screening Module:

(1) Selecting a screening model, which may be done by directly entering the ID of the model or clicking within the model list.

(2) Selecting a screening library, which may be selected from existing compound libraries, or from compound libraries uploaded by the user. The system has 12 built-in screening libraries, containing over 300,000 compounds from natural product libraries, drug libraries, covalent-binding compound libraries, protein-protein interaction small-molecule libraries, ion-channel compound libraries, and synthetic compound libraries.

Screening-Result Module:

The screening-result module includes a screening list and screening detailed information. The screening list is configured to indicate the ID of the screening model, a name of the screening library, features of the model, and starting time and ending time of the screening. The screening detailed information module includes scores and serial numbers of selected compounds. For a classification model, the scores are ranged from 0 to 1 representing the probability of having activity. For a regression model, pIC50, pKi, and pKd values will be presented wherein a compound with higher values will be predicted to have high activity.

Figure 4:
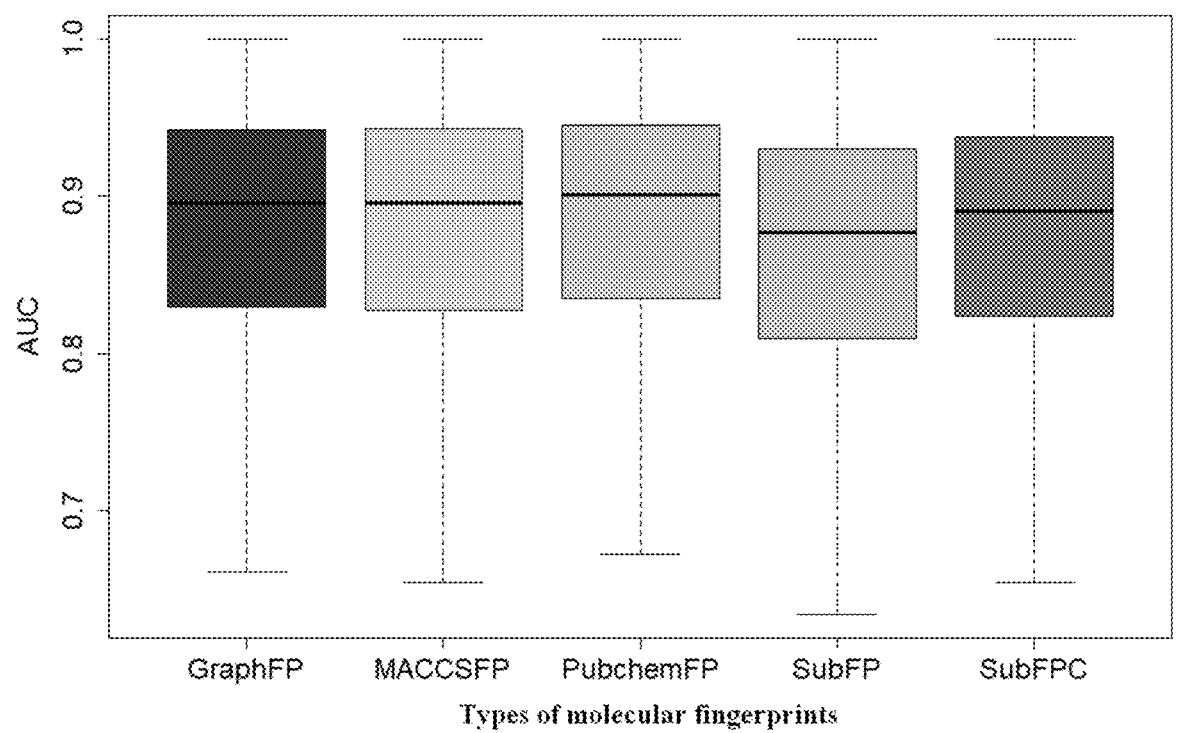
FIG. 4 is a diagram showing a virtual screening result of the high-throughput virtual drug screening system based on molecular fingerprints and deep learning of the present invention.

Virtual screening performance was tested with 966 dug targets using the AUC value and five molecular fingerprints methods. The results were as shown in FIG. 4 wherein a mean value of AUG was 0.86, indicating an excellent performance of the virtual screening.

Advantages of the Present Invention (1) Deep neural network is adopted as a virtual screening engine in the present invention, wherein the virtual screening accuracy of deep learning models is high.

(2) The compound activity database ChEMBL is adopted in the present invention. The system is applicable for 1,814 drug targets after data cleaning. Also, it is possible to upload user's own data.

(3) The present invention can rapidly realize a high-throughput virtual drug screening process, from modeling to virtual screening, which can be finished in a few minutes.

(4) The present invention enables both qualitative prediction and quantitative prediction. The system is capable of constructing classification models and regression models to qualitatively and quantitatively predict the activity of compounds.

The above description only illustrates the embodiments of the present invention, which are specific and detailed, but should not be construed as limiting the scope of the invention. It should be noted that, for a person of ordinary skill in the art, without departing from the concept of the present invention, several modifications and improvements can also be made, which all fall within the scope of the present invention. Therefore, the scope of the invention shall be subject to the appended claims.

What is claimed is:

1. A high-throughput virtual drug screening system based on molecular fingerprints and deep learning, wherein the high-throughput virtual drug screening system comprises a deep-learning model online-modeling subsystem and an online virtual-screening subsystem;

the deep-learning model online-modeling subsystem comprises an online-modeling module and a model-result module;

the online-modeling module is configured to construct a corresponding model based on a type of a model to be constructed, a drug target, the molecular fingerprints, and parameters, wherein the type of the model to be constructed, the drug target, the molecular fingerprints and the parameters are selected by a user, wherein the type of the model to be constructed comprises a qualitative classification model and a quantitative regression model;

the model-result module is configured to indicate a model list and detailed information of an individual model, wherein the model list is configured to indicate information of all models submitted by a current user, comprising serial numbers of all the models, data sources, serial numbers of drug targets, types of all the models, creation times and completion times of all the models, and status of all the models; the detailed information of the individual model comprises the parameters of the model and performance information of the model, wherein the parameters of the model and the performance information of the model are configured to indicate changes during a model performance index training process;

the online virtual-screening subsystem comprises an online-screening module and a screening-result module;

the online-screening module is configured to select a screening model and a screening library and then conduct a screening, wherein the screening model is selected by entering a serial number of the model or clicking within the model list, and the screening library is selected from existing compound libraries or from compound libraries uploaded by the user; and the screening-result module is configured to store a screening list and screening detailed information, wherein the screening list is configured to indicate a serial number of the screening model, a name of the screening library, features of the screening model, and starting time and ending time of the screening, and the screening detailed information comprises scores and serial numbers of selected compounds;

wherein the qualitative classification model is applicable for 1,251 drug targets, and the quantitative regression model is applicable for 1,814 drug targets;

wherein the high-throughput virtual drug screening system involves twelve types of the molecular fingerprints;

wherein for the qualitative classification model, the detailed information of the individual model comprises changes in loss, Accuracy, Recall, Precision, F1 score, Matthews correlation coefficient, and AUC value; and wherein for the quantitative regression model, the detailed information of the individual model comprises loss, coefficient of determination, mean squared error, root mean squared error, and mean absolute error.

2. The high-throughput virtual drug screening system based on the molecular fingerprints and deep learning according to claim 1, further comprising the compound libraries comprise natural product libraries, drug libraries, covalent-binding compound libraries, protein-protein interaction small-molecule libraries, ion-channel compound libraries, and synthetic compound libraries.

3. The high-throughput virtual drug screening system based on the molecular fingerprints and deep learning according to claim 2, further comprising for the qualitative classification model, the scores of the selected compounds are ranged from 0 to 1 representing a probability of having an activity;

for the quantitative regression model, the scores of the selected compounds comprise pIC50, pKi, and pKd values, wherein a compound with higher values is predicted to have a higher activity.

* * * * *